US011944280B2

(12) United States Patent
Betsugi et al.

(10) Patent No.: US 11,944,280 B2
(45) Date of Patent: Apr. 2, 2024

(54) ADAPTER, SURGICAL INSTRUMENT SET, AND METHOD FOR CONNECTING SURGICAL INSTRUMENT

(71) Applicant: MEDICAROID CORPORATION, Kobe (JP)

(72) Inventors: Shota Betsugi, Kobe (JP); Yu Usuki, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 835 days.

(21) Appl. No.: 16/542,264

(22) Filed: Aug. 15, 2019

(65) Prior Publication Data

US 2020/0069297 A1 Mar. 5, 2020

(30) Foreign Application Priority Data

Aug. 28, 2018 (JP) .................................. 2018-159331

(51) Int. Cl.
*A61B 17/00* (2006.01)
*A61B 34/37* (2016.01)
*A61B 34/30* (2016.01)

(52) U.S. Cl.
CPC .............. *A61B 17/00* (2013.01); *A61B 34/37* (2016.02); *A61B 2017/00115* (2013.01); *A61B 2017/00486* (2013.01); *A61B 2017/00973* (2013.01); *A61B 2034/301* (2016.02)

(58) Field of Classification Search
CPC .................... A61B 17/00; A61B 34/37; A61B 2017/00115; A61B 2017/00486; A61B 2017/00973; A61B 2034/301; A61B 46/40; A61B 46/10; A61B 2017/00477

USPC ........................................... 227/175.1–182.1
See application file for complete search history.

(56) References Cited

U.S. PATENT DOCUMENTS

| | | | | | |
|---|---|---|---|---|---|
| 3,973,179 | A | * | 8/1976 | Weber | H01M 50/204 200/332.2 |
| 4,976,173 | A | * | 12/1990 | Yang | B25F 3/00 81/177.8 |
| 5,033,552 | A | * | 7/1991 | Hu | B25F 3/00 241/37.5 |

(Continued)

FOREIGN PATENT DOCUMENTS

| | | | | |
|---|---|---|---|---|
| EP | 3232973 B1 | * | 4/2020 | ....... A61B 17/00234 |
| WO | WO-2011037394 A2 | * | 3/2011 | ............. A61B 17/00 |
| WO | WO-2017205333 A1 | * | 11/2017 | ............. A61B 18/12 |

*Primary Examiner* — Robert F Long
(74) *Attorney, Agent, or Firm* — METROLEX IP LAW GROUP, PLLC (57) ABSTRACT

An adapter for detachably connecting a surgical instrument to a robot arm of a robotic surgical system according to an embodiment may include: a base including a first surface to be attached to an attachment portion of the robot arm, a second surface, and a plurality of recesses formed in the first surface; an engagement member disposed in the base and movable between an advanced position where the engagement member is advanced into the plurality of recesses and a retracted position where the engagement member is retracted from inside the plurality of recesses; a biasing member which biases the engagement member in a direction from the retracted position to the advanced position; and an operating member to be operated to move the engagement member to the retracted position against a biasing force of the biasing member.

16 Claims, 8 Drawing Sheets

(56) References Cited

U.S. PATENT DOCUMENTS

| | | | | |
|---|---|---|---|---|
| 5,467,911 A * | 11/1995 | Tsuruta | A61B 17/0684 | 227/19 |
| 5,478,351 A * | 12/1995 | Meade | A61B 17/2909 | 606/174 |
| 6,331,181 B1 * | 12/2001 | Tierney | A61B 34/37 | 606/130 |
| 7,666,191 B2 | 2/2010 | Orban, III et al. | | |
| 7,699,855 B2 * | 4/2010 | Anderson | A61B 34/35 | 606/1 |
| 8,105,338 B2 | 1/2012 | Anderson et al. | | |
| 8,142,447 B2 | 3/2012 | Cooper et al. | | |
| 8,216,250 B2 | 7/2012 | Orban, III et al. | | |
| 8,277,473 B2 * | 10/2012 | Sunaoshi | A61B 90/90 | 606/1 |
| 8,353,436 B2 * | 1/2013 | Kasvikis | A61B 17/072 | 227/176.1 |
| 8,998,799 B2 | 4/2015 | Orban, III et al. | | |
| 9,713,509 B2 | 7/2017 | Schuh et al. | | |
| 10,182,816 B2 * | 1/2019 | Shelton, IV | H01M 10/658 | |
| 10,426,468 B2 * | 10/2019 | Contini | A61B 17/0686 | |
| 10,779,822 B2 * | 9/2020 | Yates | A61B 34/37 | |
| 10,780,539 B2 * | 9/2020 | Shelton, IV | A61B 34/76 | |
| 10,863,983 B2 * | 12/2020 | Kobayashi | A61B 17/1155 | |
| 11,369,386 B2 * | 6/2022 | Wallace | A61B 17/128 | |
| 11,490,972 B2 * | 11/2022 | Betsugi | A61B 34/25 | |
| 11,510,669 B2 * | 11/2022 | Nicholas | A61B 17/068 | |
| 11,523,509 B2 * | 12/2022 | Seow | H05K 1/148 | |
| 2005/0021018 A1 * | 1/2005 | Anderson | A61B 34/70 | 606/28 |
| 2005/0100867 A1 * | 5/2005 | Hilscher | A61C 17/221 | 15/22.1 |
| 2006/0235436 A1 * | 10/2006 | Anderson | A61B 34/71 | 606/1 |
| 2009/0182193 A1 * | 7/2009 | Whitman | A61B 1/00174 | 600/104 |
| 2009/0312603 A1 * | 12/2009 | Lam | A61B 1/018 | 600/106 |
| 2010/0069833 A1 * | 3/2010 | Wenderow | A61M 25/0147 | 604/95.01 |
| 2010/0170519 A1 * | 7/2010 | Romo | A61B 34/30 | 606/130 |
| 2010/0198220 A1 * | 8/2010 | Boudreaux | A61B 17/07207 | 606/52 |
| 2010/0274087 A1 * | 10/2010 | Diolaiti | A61B 1/00087 | 700/275 |
| 2011/0218551 A1 * | 9/2011 | Devengenzo | A61B 34/74 | 606/130 |
| 2011/0290855 A1 * | 12/2011 | Moore | A61B 34/30 | 227/176.1 |
| 2012/0239060 A1 * | 9/2012 | Orban, III | A61B 46/10 | 128/849 |
| 2013/0098968 A1 * | 4/2013 | Aranyi | A61B 17/07207 | 227/177.1 |
| 2013/0274657 A1 * | 10/2013 | Zirps | A61M 25/09041 | 604/95.01 |
| 2013/0296886 A1 * | 11/2013 | Green | B25J 15/04 | 606/130 |
| 2014/0005679 A1 * | 1/2014 | Shelton, IV | A61B 17/072 | 606/130 |
| 2014/0114334 A1 * | 4/2014 | Olson | A61B 34/37 | 606/169 |
| 2014/0249557 A1 * | 9/2014 | Koch, Jr. | A61B 17/07207 | 606/170 |
| 2014/0277334 A1 * | 9/2014 | Yu | A61B 34/30 | 901/30 |
| 2014/0305992 A1 * | 10/2014 | Kimsey | A61B 17/1155 | 227/176.1 |
| 2014/0309666 A1 * | 10/2014 | Shelton, IV | A61B 17/072 | 606/139 |
| 2015/0150547 A1 * | 6/2015 | Ingmanson | H01R 13/46 | 606/1 |
| 2015/0257841 A1 * | 9/2015 | Dachs, II | A61B 90/08 | |
| 2016/0095585 A1 * | 4/2016 | Zergiebel | A61B 34/74 | 606/1 |
| 2016/0118201 A1 * | 4/2016 | Nicholas | H01H 13/14 | 606/1 |
| 2016/0175062 A1 * | 6/2016 | Limon | B08B 3/04 | 134/116 |
| 2016/0361131 A1 * | 12/2016 | Dachs, II | A61B 1/00142 | |
| 2017/0065365 A1 * | 3/2017 | Schuh | A61B 90/50 | |
| 2017/0189020 A1 * | 7/2017 | Harris | A61B 17/07207 | |
| 2017/0196566 A1 * | 7/2017 | Sgroi | A61B 17/34 | |
| 2017/0281218 A1 * | 10/2017 | Timm | A61B 17/2909 | |
| 2017/0367782 A1 * | 12/2017 | Schuh | A61B 34/00 | |
| 2018/0049836 A1 * | 2/2018 | Shelton, IV | A61B 17/00234 | |
| 2018/0168753 A1 * | 6/2018 | Scheib | A61B 90/06 | |
| 2018/0250002 A1 * | 9/2018 | Eschbach | A61B 17/07207 | |
| 2018/0271604 A1 * | 9/2018 | Grout | B25J 9/0009 | |
| 2018/0304389 A1 * | 10/2018 | Simi | A61B 34/71 | |
| 2019/0000577 A1 * | 1/2019 | Shelton, IV | B25J 9/1682 | |
| 2019/0038279 A1 * | 2/2019 | Shelton, IV | A61B 17/068 | |
| 2019/0038281 A1 * | 2/2019 | Shelton, IV | A61B 17/29 | |
| 2019/0175287 A1 * | 6/2019 | Hill | A61B 34/30 | |
| 2019/0206565 A1 * | 7/2019 | Shelton, IV | A61B 90/37 | |
| 2019/0216554 A1 * | 7/2019 | Kapadia | A61B 34/37 | |
| 2019/0261991 A1 * | 8/2019 | Beckman | A61B 17/068 | |
| 2020/0061847 A1 * | 2/2020 | Dixon | A61B 34/30 | |
| 2020/0069297 A1 * | 3/2020 | Betsugi | A61B 17/00 | |
| 2020/0069380 A1 * | 3/2020 | Usuki | B25J 9/104 | |
| 2020/0069381 A1 * | 3/2020 | Betsugi | A61B 34/35 | |
| 2020/0069385 A1 * | 3/2020 | Ago | A61B 34/70 | |
| 2020/0305852 A1 * | 10/2020 | Ago | A61B 17/00 | |
| 2020/0305990 A1 * | 10/2020 | Ago | A61B 90/50 | |
| 2020/0305991 A1 * | 10/2020 | Ago | A61B 90/50 | |
| 2020/0315730 A1 * | 10/2020 | Zemlok | A61B 34/37 | |
| 2020/0405411 A1 * | 12/2020 | Draper | A61B 1/00149 | |
| 2021/0093398 A1 * | 4/2021 | Ago | A61B 34/30 | |
| 2021/0113283 A1 * | 4/2021 | Betsugi | A61B 34/30 | |
| 2021/0220001 A1 * | 7/2021 | Heiliger | A61B 34/37 | |
| 2021/0401531 A1 * | 12/2021 | Betsugi | A61B 46/10 | |
| 2022/0226057 A1 * | 7/2022 | Beckman | A61B 17/07207 | |
| 2022/0233257 A1 * | 7/2022 | Shelton, IV | A61B 34/30 | |
| 2023/0277268 A1 * | 9/2023 | Lau | A61B 46/10 | 128/852 |

* cited by examiner

FIG.14

ADAPTER, SURGICAL INSTRUMENT SET, AND METHOD FOR CONNECTING SURGICAL INSTRUMENT

CROSS-REFERENCE TO RELATED APPLICATIONS

This application claims priority to Japanese Patent Application No. 2018-159331 filed on Aug. 28, 2018, the entire contents of which are incorporated herein by reference.

TECHNICAL FIELD

One or more embodiments disclosed herein relate to an adapter, a surgical instrument set including the adapter, and a method for detachably connecting a surgical instrument to a robot arm.

BACKGROUND ART

An adapter for detachably connecting a surgical instrument to a robot arm of a robotic surgical system has been known (see, e.g., U.S. Pat. No. 8,142,447).

U.S. Pat. No. 8,142,447 discloses an adapter including a latch by which the adapter is detachably fixed to an attachment portion of a robot arm, and an input section which transmits a driving force of the robot arm to the surgical instrument. The adapter is fixed to the robot arm by deforming the latch and hooking the latch on the attachment portion of the robot arm.

SUMMARY

However, if the latch is hardly deformed, a greater force is necessary to deform the latch in attaching, to the robot arm, the adapter of U.S. Pat. No. 8,142,447, which is fixed to the robot arm by deforming the latch and hooking the latch on the attachment portion of the robot arm. This may cause a problem that the adapter cannot be easily attached and detached to and from the robot arm. On the other hand, if the latch is easy to be deformed, the fixing strength of the adapter to the robot arm becomes small. This may cause a problem that the adapter cannot be stably fixed to the robot arm. Thus, according to the adapter of U.S. Pat. No. 8,142,447, it may be difficult to achieve both of easily attaching and detaching the adapter to and from the robot arm, and stably fixing the adapter to the robot arm.

One or more embodiments disclosed herein are directed to an adapter for detachably connecting a surgical instrument to a robot arm of a robotic surgical system, in which the adapter is capable of being easily attached and detached to and from the robot arm, and stably fixed to the robot arm.

An adapter for detachably connecting a surgical instrument to a robot arm of a robotic surgical system according to one or more embodiments may include: a base including a first surface to be attached to an attachment portion of the robot arm, a second surface, and a plurality of recesses formed in the first surface; an engagement member disposed in the base and movable between an advanced position where the engagement member is advanced into the plurality of recesses and a retracted position where the engagement member is retracted from the plurality of recesses; a biasing member which biases the engagement member in a direction from the retracted position to the advanced position; and an operating member to be operated to move the engagement member to the retracted position against a biasing force of the biasing member.

A surgical instrument set according to one or more embodiments may include: an adapter to be attached to a robot arm of a robotic surgical system; and a surgical instrument to be attached to the adapter. The adapter may include: a base including a first surface to be attached to an attachment portion of the robot arm, a second surface different from the first surface, and a plurality of recesses formed in the first surface; an engagement member disposed in the base and movable between an advanced position where the engagement member is advanced into the plurality of recesses and a retracted position where the engagement member is retracted from the plurality of recesses; a biasing member which biases the engagement member in a direction from the retracted position to the advanced position; and an operating member to be operated to move the engagement member to the retracted position against a biasing force of the biasing member. The surgical instrument may have an attachment surface to be attached to the second surface of the adapter.

One or more embodiments is directed to a method for connecting a surgical instrument, in which the adapter may include: a base including a first surface to be attached attachment to an attachment portion of the robot arm, a second surface to which an attachment surface of the surgical instrument is attached, and a plurality of recesses formed in the first surface; an engagement member movable between an advanced position where the engagement member is advanced into the plurality of recesses and a retracted position where the engagement member is retracted from the plurality of recesses; a biasing member which biases the engagement member in a direction from the retracted position to the advanced position; and an operating member to be operated to move the engagement member to the retracted position against a biasing force of the biasing member. The method may include: moving the engagement member to the retracted position with the operating member; attaching the first surface of the adapter in which the engagement member has been moved to the retracted position, to the attachment portion of the robot arm; moving the engagement member to the advanced position by the biasing member; and attaching the attachment surface of the surgical instrument to the second surface of the adapter.

DETAILED DESCRIPTION

One or more embodiments will be described below with reference to the drawings.

(Configuration of Robotic Surgical System)

Configurations of a robotic surgical system 100 according to an embodiment will be described with reference to FIGS. 1 and 2.

Figure 1:
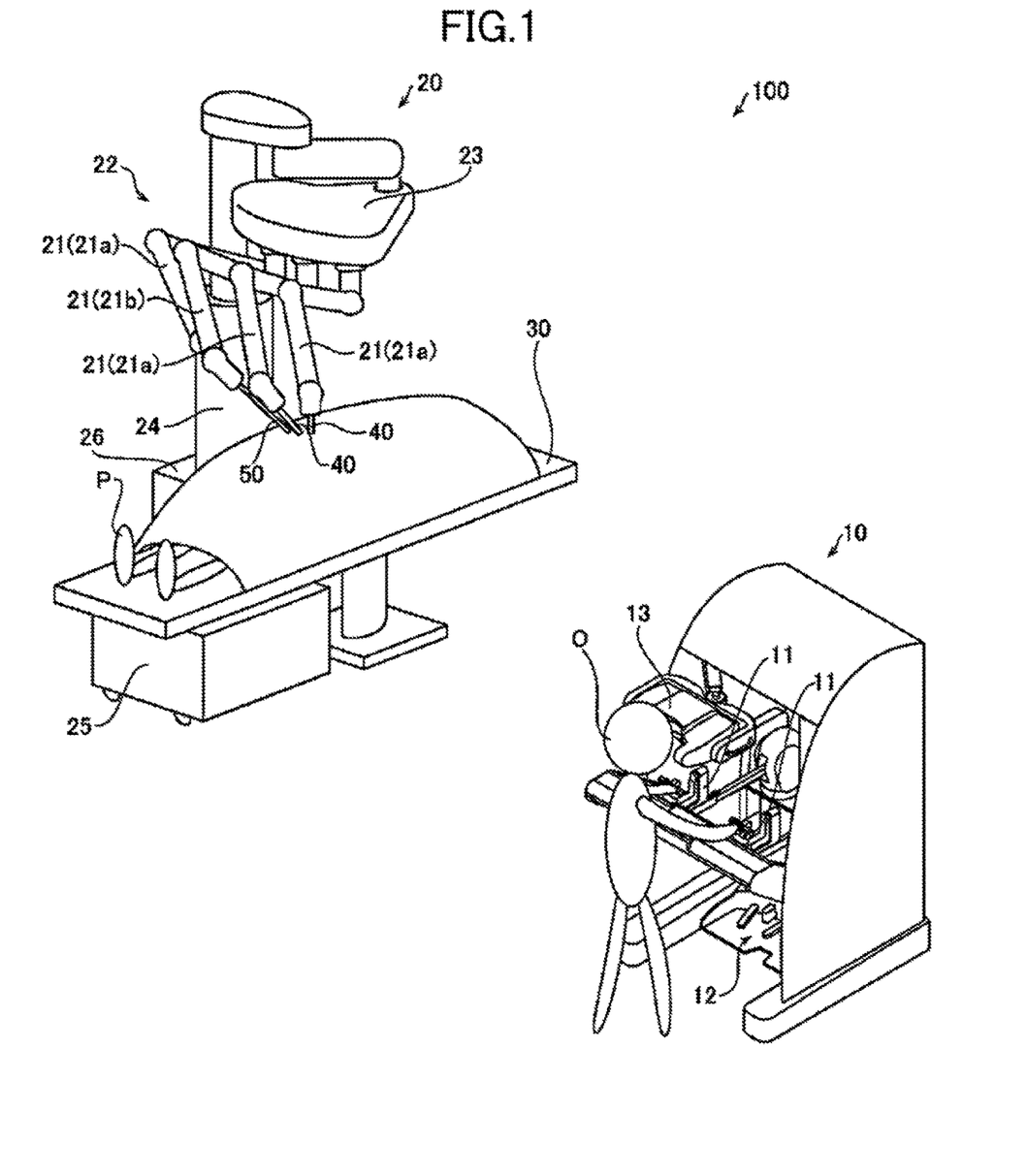
FIG. 1 is a diagram schematically illustrating a view of a robotic surgical system according to an embodiment.

As illustrated in FIG. 1, the robotic surgical system 100 includes a remote control apparatus 10 and a patient-side apparatus 20. The remote control apparatus 10 is used to remotely operate medical equipment provided for the patient-side apparatus 20. When an operator O, who is a surgeon, enters a movement type instruction to be executed by the patient-side apparatus 20 to the remote control apparatus 10, the remote control apparatus 10 transmits the movement type instruction to the patient-side apparatus 20 via a controller 26. The patient-side apparatus 20 then handles the medical equipment, such as a surgical instrument 40 or an endoscope 50 attached to a robot arm 21, in response to the movement type instruction transmitted from the remote control apparatus 10. A minimally invasive operation is performed in this manner.

The patient-side apparatus 20 constitutes an interface through which a surgery is performed on a patient P. The patient-side apparatus 20 is arranged beside a surgical table 30 on which the patient P lies. The patient-side apparatus 20 has a plurality of robot arms 21. An endoscope 50 is attached to one of the robot arms 21 (i.e., the robot arm 21(21b)). Surgical instruments 40 are attached to the other robot arms 21(21a). The robot arms 21 are supported by the same platform 23. Each of the robot arms 21 has a plurality of joints. A driving section including a servomotor and a position detector such as an encoder are provided for each joint. Each robot arm 21 is configured to be controlled such that the medical equipment attached to the robot arm 21 make a desired movement in response to a driving signal given via the controller 26.

The platform 23 is supported by a positioner 22 placed on the floor of the operating room. The positioner 22 includes a column 24 having a lifting shaft adjustable in a vertical direction, and the lifting shaft is coupled to a base 25 having wheels and movable on the floor surface.

The surgical instrument 40 as the medical equipment detachably attached to a distal end portion of the robot arm 21a. The surgical instrument 40 includes a housing 43 (see FIG. 4) attached to the robot arm 21a, an elongated shaft 42 (see FIG. 4), and an end effector 41 (see FIG. 4) attached to a distal end portion of the shaft 42. Examples of the end effector 41 include, but are not limited to, a grasping forceps, scissors, a hook, a high-frequency knife, a snare wire, a clamp, and a stapler, and may include various types of treatment tools. In a surgery using the patient-side apparatus 20, each of the robot arms 21a introduces the surgical instrument 40 into the body of the patient P through a cannula (a trocar) retained on the body surface of the patient P. The end effector 41 of the surgical instrument 40 is placed in the vicinity of the surgical site.

The endoscope 50 as the medical equipment is detachably attached to a distal end portion of the robot arm 21b. The endoscope 50 takes images in the body cavity of the patient P. The images taken are output to the remote control apparatus 10. Examples of the endoscope 50 include a 3D endoscope capable of taking three-dimensional images, and a 2D endoscope. In a surgery using the patient-side apparatus 20, the robot arm 21b introduces the endoscope 50 into the body of the patient P through a trocar retained on the body surface of the patient P. The endoscope 50 is placed in the vicinity of the surgical site.

The remote control apparatus 10 constitutes an interface with the operator O. The remote control apparatus 10 serves as a device through which the operator O operates the medical equipment attached to each robot arm 21. That is, the remote control apparatus 10 is configured to be capable of transmitting, to the patient-side apparatus 20, the movement type instruction that has been input by the operator O and that should be executed by the surgical instrument 40 and the endoscope 50, via the controller 26. The remote control apparatus 10 is installed beside the surgical table 30 so that the operator can check the condition of the patient P while operating the master, for example. The remote control apparatus 10 may be configured, for example, to wirelessly transmit the movement type instruction, and may be installed in a room different from the operating room where the surgical table 30 is placed.

The term "movement type" to be performed by the surgical instrument 40 may refer to the type of movement (a series of positions and orientations) of the surgical instrument 40 and the type of movement executed by the function of the respective surgical instruments 40. For example, if the surgical instrument 40 is a grasping forceps, the movement type to be performed by the surgical instrument 40 includes positions of rolling and pitching of a wrist of the end effector 41, and opening and closing the jaws. If the surgical instrument 40 is a high-frequency knife, the movement type to be executed by the surgical instrument 40 may include vibration of the high-frequency knife, specifically, a current supply to the high-frequency knife. If the surgical instrument 40 is a snare wire, the movement type to be performed by the surgical instrument 40 may include tightening, and releasing from the tightening. In addition, the movement type may include a movement of burning off a target site of the surgery, using a bipolar or a monopolar to which an electric current is supplied.

Examples of the movement type to be performed by the endoscope 50 include positioning, and determination of the orientation, of the tip end of the endoscope 50, or setting of zoom magnification of the endoscope 50.

Figure 2:
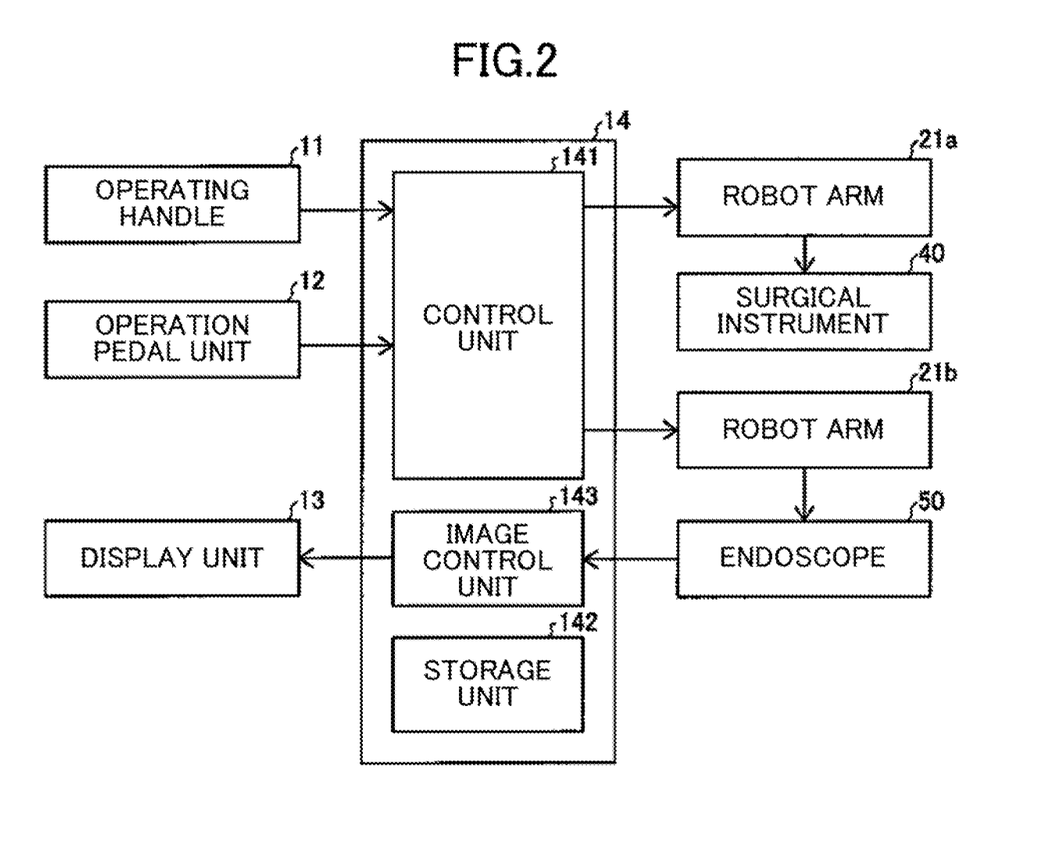
FIG. 2 is a block diagram illustrating a view of a control configuration of the robotic surgical system according to an embodiment.

As illustrated in FIGS. 1 and 2, the remote control apparatus 10 includes an operating handle 11, an operation pedal unit 12, a display unit 13, and a control device 14.

The operating handle 11 is intended to remotely operate the medical equipment attached to each robot arm 21. Specifically, the operating handle 11 accepts the operation conducted by the operator O to control the medical equipment (i.e., the surgical instrument 40 and the endoscope 50). The operating handle 11 includes two operating handles 11 arranged in the horizontal direction. Specifically, one of the two operating handles 11 is operated by the right hand of the operator O, and the other operating handle 11 is operated by the left hand of the operator O.

The operating handle 11 is arranged to extend from the back side to the front side of the remote control apparatus 10. The operating handle 11 is configured to be movable within a predetermined three-dimensional operation area A. Specifically, the operating handle 11 is configured to be movable up and down directions, the leftward and rightward directions, and the forward and backward directions.

The remote control apparatus 10 and the patient-side apparatus 20 constitute a master-slave system in controlling the movements of the robot arms 21a and the robot arm 21b. Specifically, the operating handle 11 serves as a master controlling element in the master-slave system, and the robot arms 21a and the robot arm 21b to which the medical equipment is attached serve as slave moving elements. When the operator O operates the operating handle 11, the movement of the robot arms 21a or the robot arm 21b is controlled so that the distal end portion of each robot arm 21a (i.e., the end effector 41 of surgical instrument 40) or the distal end portion of the robot arm 21b (i.e., the endoscope 50) will trace the movement of the operating handle 11 and shift accordingly.

The patient-side apparatus 20 is configured to control the movements of the respective robot arms 21a according to a movement scale factor which has been set. For example, in a case in which the movement scale factor has been set to be ½, the end effector 41 of the surgical instrument 40 is controlled to shift by one half (½) of a distance by which the operating handle 11 has shifted. As a result, precise surgery can be accurately performed.

The operation pedal unit 12 includes a plurality of pedals for executing the function related to the medical equipment. The plurality of pedals include a coagulation pedal, a cutting pedal, a camera pedal, and a clutch pedal. The plurality of pedals are operated by the foot of the operator O.

The coagulation pedal enables the operation of coagulating the surgical site using the surgical instrument 40. Specifically, when the coagulation pedal is operated, a voltage for coagulation is applied to the surgical instrument 40, thereby coagulating the surgical site. The cutting pedal enables the operation of cutting the surgical site using the surgical instrument 40. Specifically, when the cutting pedal is operated, a voltage for the cutting is applied to the surgical instrument 40, thereby cutting the surgical site.

The camera pedal is used to change the position and orientation of the endoscope 50 taking images of the body cavity. Specifically, the camera pedal validates the operation of the endoscope 50 through the operating handle 11. That is, while the camera pedal is pressed down, the position and orientation of the endoscope 50 can be changed by using the operating handle 11. For example, the endoscope 50 is operated using both of the left and right operating handles 11. Specifically, the endoscope 50 rotates when the right and left operating handles 11 rotate about a midpoint between the left and right operating handles 11. The endoscope 50 moves forward when the left and right operating handles 11 are pushed forward. The endoscope 50 moves backward when the left and right operating handles 11 are pulled backward. The endoscope 50 moves up and down, and leftward and rightward when the left and right operating handles 11 are moved up and down, and leftward and rightward.

The clutch pedal is used to temporarily block the connection for operation between the robot arm 21 and the operating handle 11 to stop the movement of the surgical instrument 40. Specifically, while the clutch pedal is pressed down, the robot arm 21 of the patient-side apparatus 20 does not move even if the operating handle 11 is moved. For example, when the operating handle 11 comes close to the end of the movable range thereof, the clutch pedal is pressed down to temporarily block the connection for operation so that the operating handle 11 can be returned to the center position. When the clutch pedal is no longer pressed down, the robot arm 21 and the operating handle 11 are connected again, and the operating handle 11 can be operated again at around the center position.

The display unit 13 can display the images taken by the endoscope 50. The display unit 13 includes a scope type display unit or a non-scope type display unit. The scope type display unit is, for example, a display unit which an operator looks into. The non-scope type display unit represents a concept that includes an open display unit having a flat screen which an operator does not look into, just like a display of a common personal computer.

In a case in which the scope type display unit is attached, a 3D image taken by the endoscope 50 attached to the robot arm 21b of the patient-side apparatus 20 is displayed. Also in a case in which the non-scope type display unit is attached, a 3D image taken by the endoscope 50 provided in the patient-side apparatus 20 is displayed. In the case in which the non-scope type display unit is attached, a 2D image taken by the endoscope 50 provided in the patient-side apparatus 20 may be displayed.

As illustrated in FIG. 2, the control device 14 includes, for example, the control unit 141 including an arithmetic unit such as a CPU, a storage unit 142 including a memory such as a ROM and a RAM, and an image control unit 143. The control device 14 may be comprised of a single controller which provides centralized control, or may be configured as a plurality of controllers which work in cooperation with each other and provide distributed control. The control unit 141 determines whether the movement type instruction input through the operating handle 11 is a movement type instruction to be executed by the robot arm 21a, or a movement type instruction to be executed by the endoscope 50, in accordance with the state of the operation pedal unit 12. If the control unit 141 determines that the movement type instruction input through the operating handle 11 is a movement type instruction to be executed by the surgical instrument 40, the control unit 141 transmits this movement type instruction to the robot arm 21a. In response, the robot arm 21a is driven, as a result of which the operation of the surgical instrument 40 attached to the robot arm 21a is controlled.

Alternatively, if the control unit 141 determines that the movement type instruction input through the operating handle 11 is a movement type instruction to be executed by the endoscope 50, the control unit 141 transmits the movement type instruction to the robot arm 21b. In response, the robot arm 21b is driven, as a result of which the operation of the endoscope 50 attached to the robot arm 21b is controlled.

The storage unit 142 stores, for example, control programs corresponding to the types of the surgical instrument 40. The control unit 141 reads the control program in accordance with the type of the surgical instrument 40 attached, thereby allowing the movement instruction entered through the operating handle 11 and/or operation pedal unit 12 of the remote control apparatus 10 to cause each surgical instrument 40 to perform a suitable operation.

The image control unit 143 transmits images taken by the endoscope 50 to the display unit 13. The image control unit 143 processes or corrects the image as needed.

(Configurations of Adapter and Surgical Instrument)

Configurations of an adapter 60 and the surgical instrument 40 according to an embodiment will be described with reference to FIGS. 3 to 11.

Figure 3:
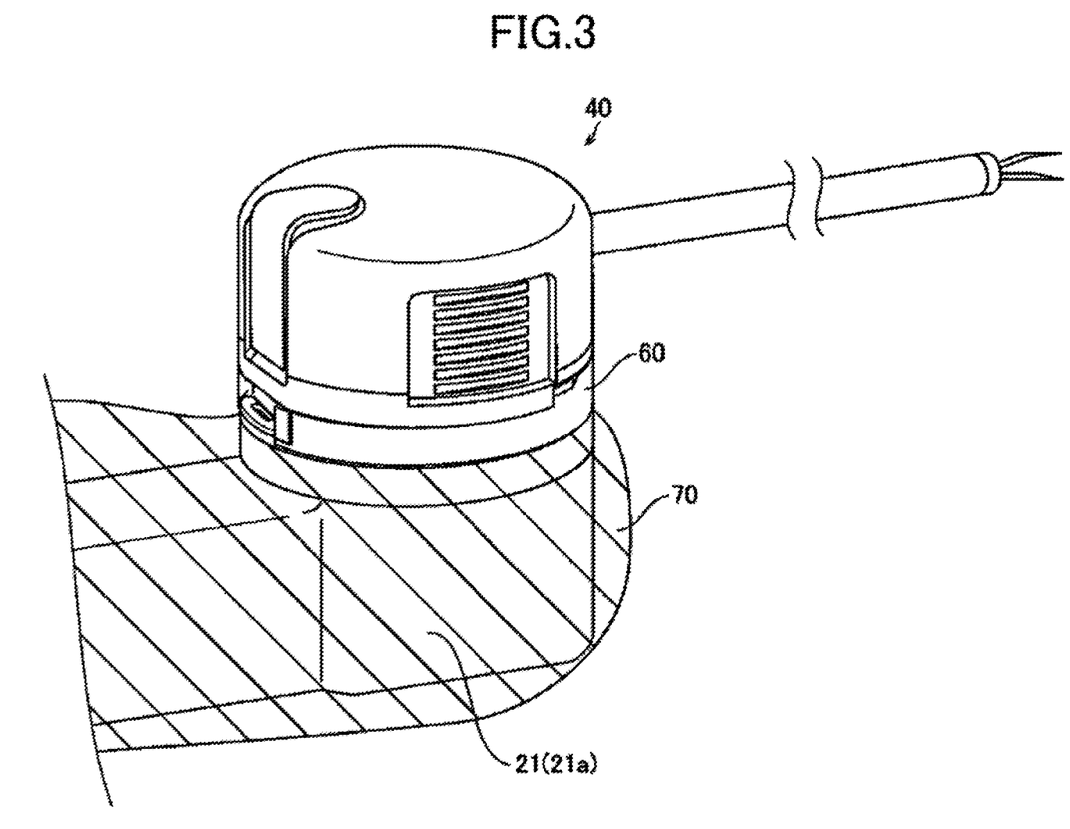
FIG. 3 is a diagram illustrating a perspective view of the state in which a surgical instrument is attached to a robot arm according to an embodiment via an adapter.

As illustrated in FIG. 3, the robot arm 21 is covered with a drape 70 because the robot arm 21 is used in a clean zone. In an operating room, a cleaning procedure is carried out to prevent surgery incisions and medical equipment from being infected and contaminated with pathogenic bacteria, foreign substances, or the like. A clean zone and a contaminated zone, which is a zone other than the clean zone, are defined in this cleaning procedure. The surgical site is positioned in the clean zone. Surgery team members, including the operator O, take good care so that only a disinfected object is placed in the clean zone during the surgery, and sterilize the object placed in the contaminated zone when it needs to be moved to the clean zone. Similarly, if the surgery team members, including the operator O, have put their hands in the contaminated zone, they sterilize their hands before they directly touch an object placed in the clean zone. The instrument to be used in the clean zone is sterilized, or is covered with a sterilized drape 70.

The drape 70 is positioned between the robotic arm 21 and the surgical instrument 40. Specifically, the drape 70 is positioned between the adapter 60 and the robotic arm 21. The adapter 60 is attached to the attachment portion 211 of the robot arm 21 via the drape 70. That is, the adapter 60 is a drape adapter for tucking the drape 70 between the adapter 60 and the robot arm 21a. The surgical instrument 40 is attached to the adapter 60. The robot arm 21 transmits power to the surgical instrument 40 via the adapter 60 in order to drive the end effector 41 of the surgical instrument 40.

Figure 4:
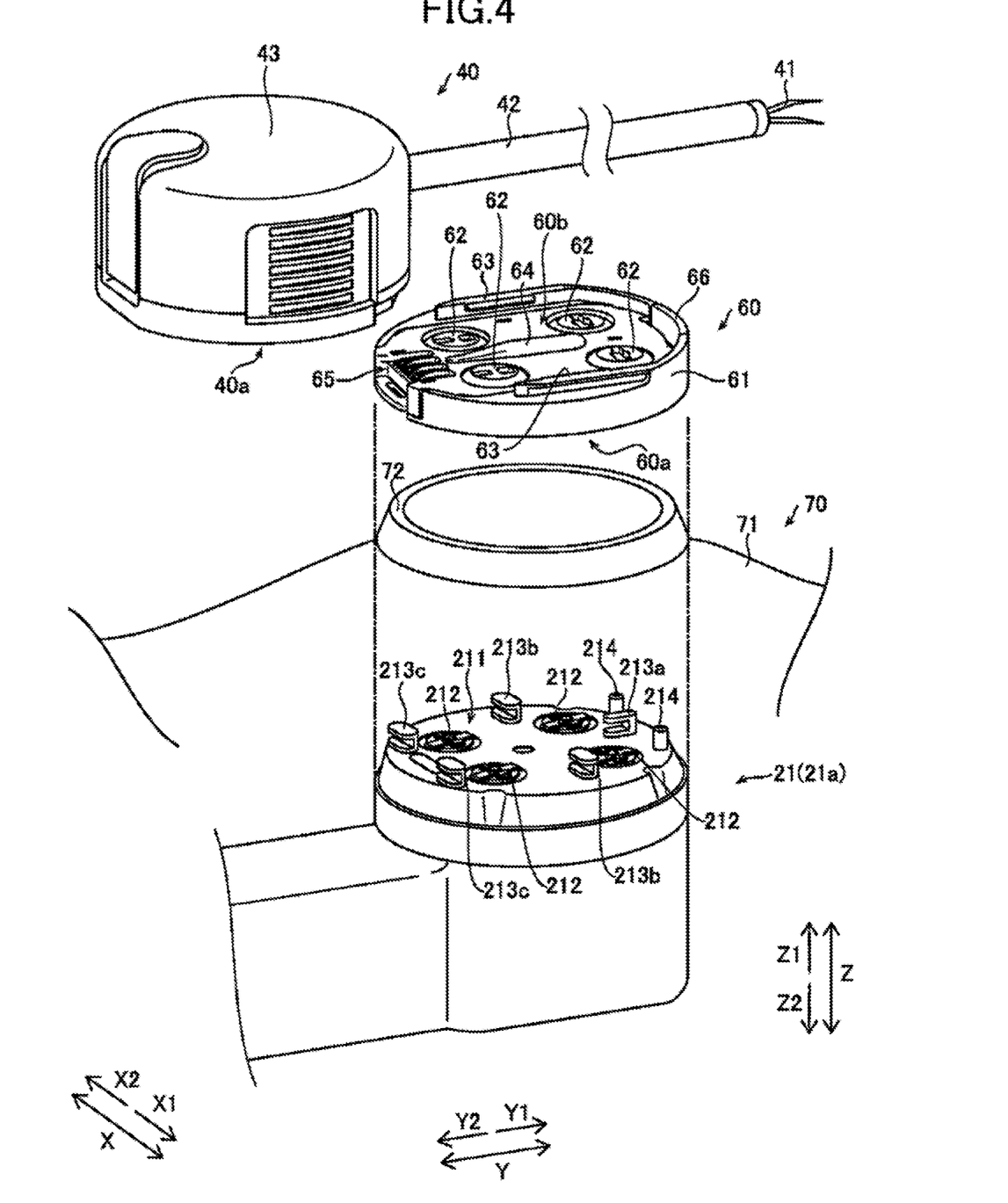
FIG. 4 is a diagram illustrating a perspective view of the state in which the surgical instrument and the adapter are detached from the robot arm according to an embodiment.
Figure 5:
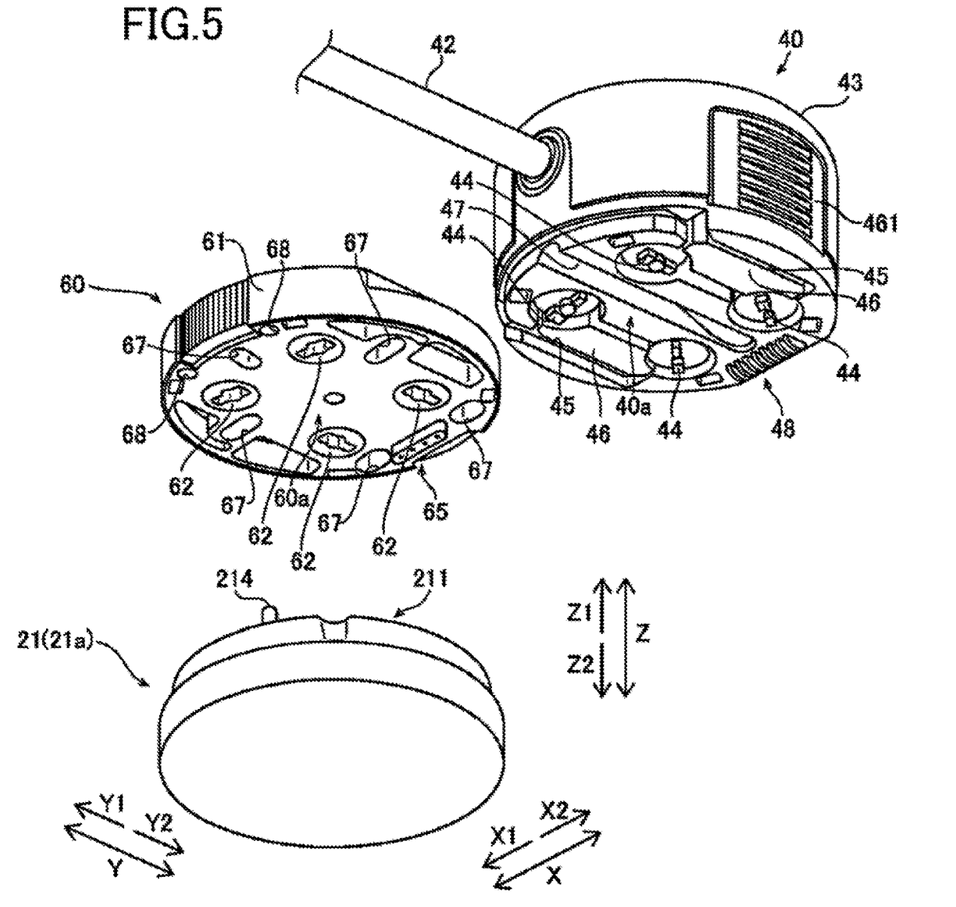
FIG. 5 is a diagram illustrating a perspective view of the adapter, the surgical instrument, and an attachment portion of the robot arm according to an embodiment as viewed from below.

As illustrated in FIG. 4, the adapter 60 includes a base 61, a plurality of drive power transmission members 62, guide rails 63, a leading guide rail 64, an electrode array 65, and an arm engagement member 66. As illustrated in FIG. 5, the adapter 60 includes a plurality of recesses 67 and a plurality of positioning holes 68. A first surface 60a of the adapter 60 toward the Z2 direction is attached to the robot arm 21a. The surgical instrument 40 is attached to a second surface 60b of the adapter 60 toward the Z1 direction.

As illustrated in FIG. 5, an attachment surface 40a of the housing 43 of the surgical instrument 40 toward the Z2 direction is attached to the adapter 60. The surgical instrument 40 includes a plurality of driven sections 44, two guide grooves 45, two movable members 46, a leading guide groove 47, and an electrode array 48.

As illustrated in FIG. 4, the drape 70 has a main body 71 and an attachment portion 72. The main body 71 is formed to be like a film. The attachment portion 72 is resin molded. The attachment portion 72 has a through hole, through which the robot arm 21a and the adapter 60 are engaged with each other. The through hole may be formed so as to correspond to each engaging portion. Alternatively, the through hole may be formed so as to correspond to a plurality of engaging portions.

The adapter 60 is attached to the attachment portion 211 of the robot arm 21. The robot arm 21 includes a driving member 212, an engagement projecting portion 213, and a boss 214. The engagement projecting portion 213 includes engagement projecting portions 213a, 213b, and 213c. Two engagement projecting portions 213b and two engagement projecting portions 213c are provided.

Each of the plurality of engagement projecting portions 213 has a groove 2131. The engagement projecting portions 213 are intended for engagement with the adapter 60. Specifically, engagement portions 661 of an engagement member 66 of the adapter 60 engages with the groove 2131 of a corresponding one of the engagement projecting portions 213 of the robot arm 21. Each of the plurality of grooves 2131 is open toward the Y2 direction.

As illustrated in FIG. 5, the plurality of driven sections 44 of the surgical instrument 40 are driven to rotate, thereby actuating the end effector 41. Specifically, the driven sections 44 and the end effector 41 are connected by one or more wires which pass through the shaft 42. The one or more wires are to be pulled by the rotation of the driven sections 44. The end effector 41 is actuated by pulling at least one of the one or more wires. The driven sections 44 are connected to the shaft 42 by gears in the housing 43. The rotation of the driven sections 44 causes the shaft 42 to rotate.

There are four driven sections 44, for example. The rotation of one driven section 44 causes the shaft 42 to rotate. The rotation of the other three driven sections 44 actuates the end effector 41. The four driven sections 44 are arranged such that two driven sections are arranged toward the X direction, and the other two driven sections are arranged toward the Y direction.

The guide groove 45 extends along the Y direction. Two guide grooves 45 are provided so as to be opposed to each other in the X direction. The two guide grooves 45 are arranged approximately parallel to each other. The guide rails 63 of the adapter 60 are inserted into each of the guide grooves 45, thereby guiding the attachment to the adapter 60. The width of the guide groove 45 changes as the movable member 46 moves in the X direction. That is, the width of the guide groove 45 increases as the movable member 46 moves toward the inside in the X direction. The width of the guide groove 45 decreases as the movable member 46 moves toward the outside in the X direction. The movable member 46 is biased toward the direction (i.e., outward) which narrows the width of the guide groove 45. Specifically, the movable member 46 is biased by a spring. Pushing of a button 461 by an operator causes the movable member 46 to move toward the direction (i.e., inward) which increases the width of the guide groove 45.

The leading guide groove 47 extends along the Y direction. The leading guide groove 47 is disposed between the two guide grooves 45. The leading guide groove 47 extends approximately parallel to the two guide grooves 45. The leading guide groove 47 is arranged approximately in the middle of the attachment surface 40a in the X direction.

The electrode array 48 is connected to the robot arm 21 via the electrode array 65 of the adapter 60. The electrode array 48 is connected to a board provided in the housing 43. That is, the board of the surgical instrument 40 and the robot arm 21 are connected to each other by the attachment of the surgical instrument 40 to the robot arm 21 via the adapter 60. The board in the housing 43 is used to manage the type of the surgical instrument 40, the number of usage time of the surgical instrument 40, and so on.

Figure 6:
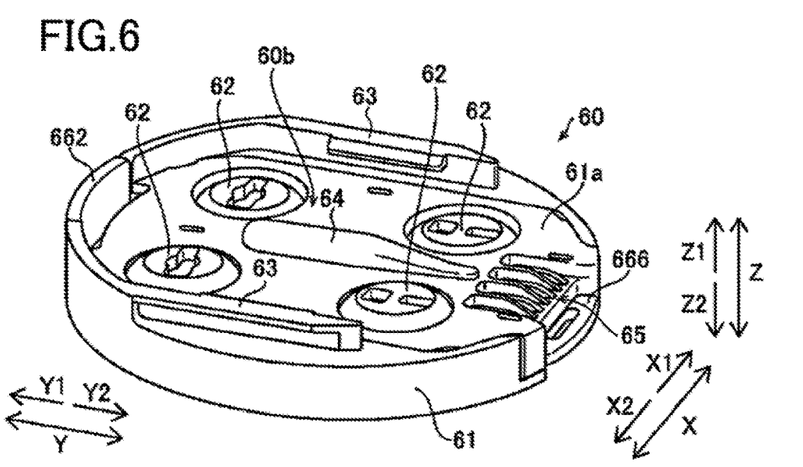
FIG. 6 is a diagram illustrating a perspective view of the adapter according to an embodiment as viewed from above.

As illustrated in FIGS. 4 to 6, the adapter 60 is provided for detachably connecting the surgical instrument 40 to the robotic arm 21a of the robotic surgical system 100. The base 61 includes a first surface 60a for attachment to the robot arm 21a, and a second surface 60b to which the attachment surface 40a of the surgical instrument 40 is attached.

The drive power transmission members 62 are rotatably disposed in the base 61. Specifically, the drive power transmission members 62 are rotatable about a rotational axis extending in the Z direction. That is, the drive power transmission members 62 are rotatable about the rotational axis perpendicular to the first surface 60a and the second surface 60b. The drive power transmission members 62 transmit the rotation of the plurality of driving members 212, which are provided for the attachment portion 211 of the robot arm 21a, to the plurality of driven sections 44 provided for the surgical instrument 40. A multiple number of drive power transmission members 62 are provided so as to correspond to the respective driving members 212 of the robot arm 21a and the respective driven sections 44 of the surgical instrument 40. The plurality of drive power transmission members 62 are disposed at positions corresponding to the respective driving members 212 of the robot arm 21a and the respective driven sections 44 of the surgical instrument 40.

The guide rails 63 are formed on the second surface 60b. Each of the guide rails 63 extends along the Y direction. The guide rails 63 include two guide rails 63 provided so as to be opposed to each other in the X direction. The two guide rails 63 are arranged approximately parallel to each other. The two guide rails 63 are formed so as to correspond to the two guide grooves 45 arranged approximately parallel to each other in the attachment surface 40a of the surgical instrument 40. The guide grooves 45 in the attachment surface 40a are brought to, and slid along, the respective guide rails 63 on the second surface 60b, thereby guiding the surgical instrument 40 to a position where the plurality of drive power transmission members 62 correspond to the plurality of driven sections 44 provided in the attachment surface 40a.

The leading guide rail 64 is formed on the second surface 60b. The leading guide rail 64 extends along the Y direction. The leading guide rail 64 is disposed between the two guide rails 63. The leading guide rail 64 extends approximately parallel to the two guide rails 63. The leading guide rail 64 is arranged approximately in the middle of the second surface 60b in the X direction. The leading guide rail 64 is formed so as to correspond to the leading guide groove 47 formed in the attachment surface 40a. That is, the leading guide rail 64 leads the two guide rails 63 in guiding the surgical instrument 40.

The electrode array 65 is connected to the electrode array 48 of the surgical instrument 40 and the robot arm 21.

Figure 7:
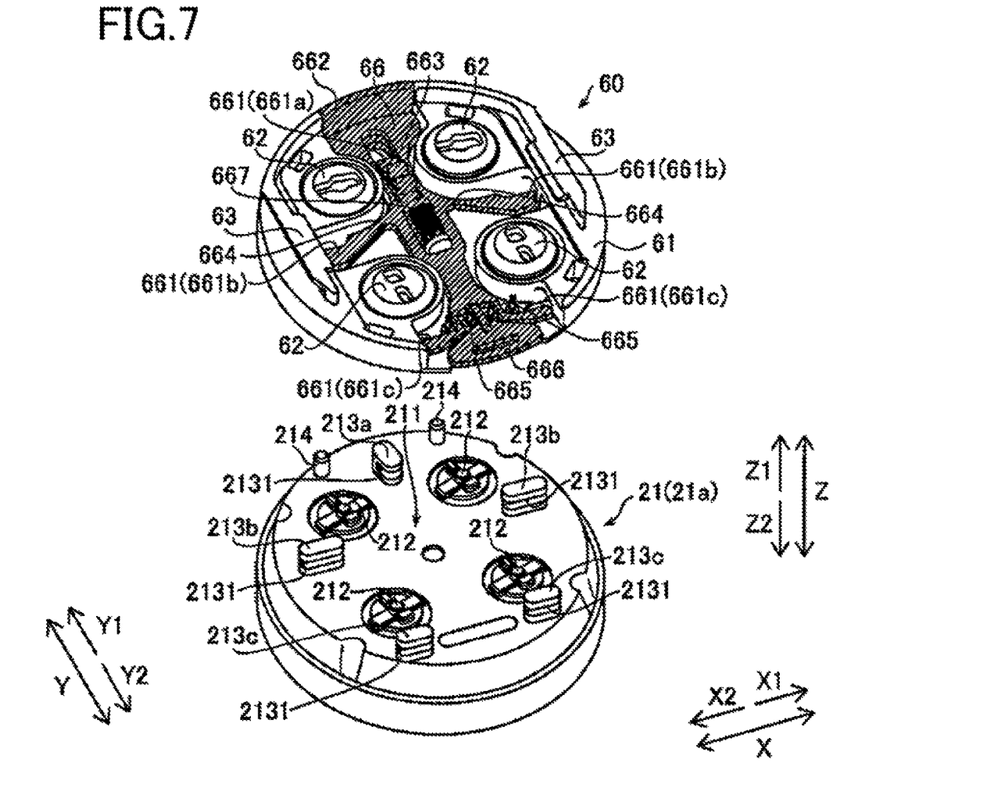
FIG. 7 is a diagram illustrating a perspective view of the state in which the adapter is detached from the attachment portion of the robot arm according to an embodiment.
Figure 8:
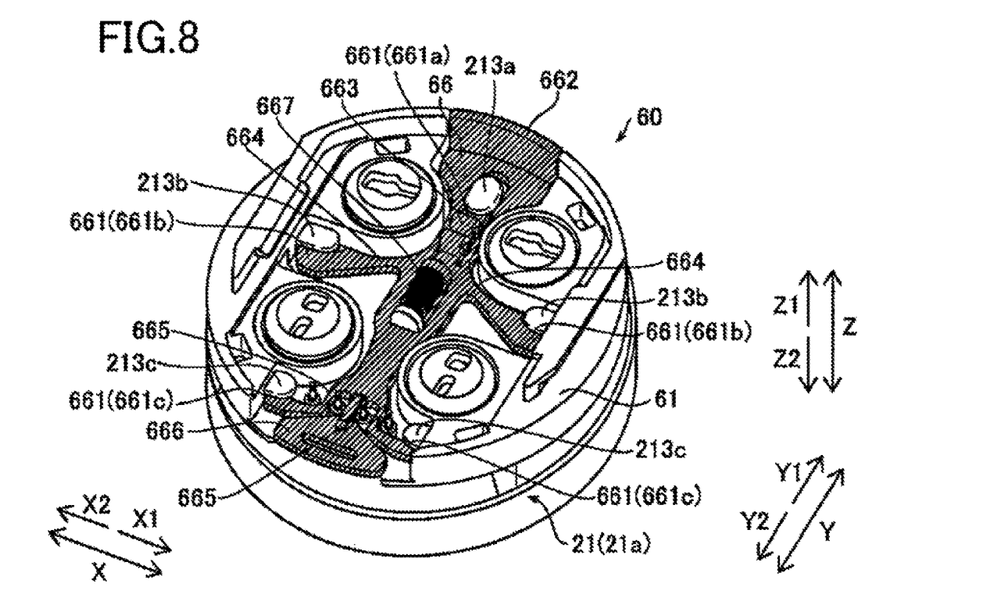
FIG. 8 is a diagram illustrating a perspective view of the state in which the adapter is attached to the attachment portion of the robot arm according to an embodiment.

The arm engagement member 66 engages with the engagement projecting portion 213 of the robot arm 21. Specifically, the arm engagement member 66 engages with the engagement projecting portions 213 in the state where the engagement projecting portions 213 of the robot arm 21 are inserted, in the Z direction, in the recesses 67 formed in the first surface 60a of the adaptor 60. As illustrated in FIGS. 7 and 8, the arm engagement member 66 includes an engagement member 661, an operating member 662, a bent portion 663, a narrow width portion 664, and a gripping portion 666. The arm engagement member 66 is biased in the Y1 direction by a first biasing member 667. The engagement member 661 includes engagement portions 661a, 661b, and 661c. Two engagement portions 661b and two engagement portions 661c are provided.

The engagement member 661 of the arm engagement member 66 is movable in the Y direction with respect to the base 61 of the adaptor 60. When the engagement member 661 is moved by an operator or a user in the Y1 direction in the state where the engagement projecting portions 213 of the robot arm 21 are inserted in the recesses 67 of the adaptor 60, the engagement member 661 is engaged with the engagement projecting portion 213. When the arm engagement member 66 is moved in the Y2 direction, in the state where the engagement projecting portions 213 of the robot arm 21 are inserted in the recesses 67 of the adaptor 60, the arm engagement member 66 is disengaged from the engagement projecting portion 213. In an embodiment, the engagement member 661 of the arm engagement member 66 is movable between an advanced position (see FIG. 11), to which the engagement member 661 is advanced in the direction (i.e., the Y direction) intersecting with the direction (i.e., the Z direction) in which the first surface 60a and the attachment portion 211 of the robot arm 21a face each other, and a retracted position (see FIG. 10) where the engagement member 661 is retracted from the plurality of recesses 67. The first biasing member 667, provided between the base 61 and the engagement member 66, biases the engagement member 661 in the direction from the retracted position to the advanced position (i.e., the Y1 direction). The operating member 662 of the arm engagement member 66 is provided on the second surface 60b of the base 61, and is intended to move the engagement member 661 to the retracted position against the biasing force of the first biasing member 667. The operating member 662 is operated by being pushed in the Y2 direction by the operator.

This configuration enables switching between the engaged state and the disengaged state of the engagement member 661 by moving the engagement member 661 along the direction intersecting with the direction in which the first surface 60a and the attachment portion 211 of the robot arm 21a face each other (i.e., along the first surface 60a (i.e., in the Y direction) which is different from the engagement direction (i.e., the Z direction) of the adapter 60 and the robot arm 21a). Thus, the adapter 60 can be stably fixed to the robot arm 21a without the need to increase the biasing force of the first biasing member 667 with respect to the engagement member 661. Without the need to increase the biasing force of the first biasing member 667 with respect to the engagement member 661, the operator does not need to apply great force to operate the operating member 662. This means that the adapter 60 can be easily attached and detached to and from the robot arm 21a. Consequently, the adapter 60 for detachably connecting the surgical instrument 40 to the robot arm 21a of the robotic surgical system 100 can be easily attached and detached to and from the robot arm 21a, and be stably fixed to the robot arm 21a.

The arm engagement member 66 is configured such that the movement of the engagement member 661 by the operating member 662 is restricted in the state in which the first surface 60a of the adapter 60 is attached to the attachment portion 211 of the robot arm 21 and the surgical instrument 40 is attached to the second surface 60b. This configuration reduces the possibility that the robot arm 21a and the adapter 60 are detached from each other in the state in which the surgical instrument 40 is attached. The surgical instrument 40 is therefore less likely to come off the robot arm 21a together with the adapter 60.

Specifically, the operating member 662 protrudes toward the surgical instrument 40 from the second surface 60b. In the state in which the surgical instrument 40 is attached to the second surface 60b, the operating member 662 is in contact with the surgical instrument 40, and the movement of the operating member 662 is therefore restricted. That is, when the surgical instrument 40 is slid in the Y direction and attached to the adapter 60, an edge portion, toward the Y1 direction, of the housing 43 of the surgical instrument 40 comes into contact with the operating member 662. The surgical instrument 40, once fixed to the adapter 60, is no longer capable of moving in the Y direction, which restricts the movement of the operating member 662 in the Y direction, as well. Thus, in the state in which the surgical instrument 40 is attached, the surgical instrument 40 restricts the movement of the operating member 662, which eliminates the need to provide another member for restricting the movement of the operating member 662.

The engagement member 661 is configured to engage with the groove 2131 formed in each of the plurality of engagement projecting portions 213 of the robot arm 21a. This configuration allows the engagement member 661 to be engaged with the grooves 2131 of the plurality of engagement projecting portions 213 in the state in which the plurality of engagement projecting portions 213 projecting from the attachment portion 211 of the robot arm 21a are inserted in the plurality of recesses 67 of the adapter 60. The adapter 60 can thus be more stably fixed to the robot arm 21a.

Specifically, the engagement projecting portion 213a provided on the attachment portion 211 of the robot arm 21a at a position near an edge portion toward the Y1 direction of the Y direction engages with the engagement portion 661a of the arm engagement member 66 near an edge portion toward the Y1 direction of the Y direction. The two engagement projecting portions 213b provided on the attachment portion 211 of the robot arm 21a at positions near the middle in the Y direction respectively engage with the two engagement portions 661b of the arm engagement member 66 near the middle in the Y direction. The two engagement projecting portions 213c provided on the attachment portion 211 of the robot arm 21a at positions near an edge portion toward the Y2 direction of the Y direction respectively engage with the two engagement portions 661c of the arm engagement member 66 near an edge portion toward the Y2 direction of the Y direction.

The engagement member 661 is configured such that the plurality of engagement portions 661a to 661c, which engage with the plurality of engagement projecting portions 213 of the robot arm 21a, are integrally formed portions. This configuration contributes to reducing the number of parts, as compared to the case in which the plurality of engagement portions 661a to 661c which engage with the plurality of engagement projecting portions 213 are provided independently from one another.

The operating member 662 moves the plurality of engagement portions 661a to 661c in an integrated manner. This configuration enables switching between the engaged state and the disengaged state of the plurality of engagement portions 661a to 661c at once by operating the single operating member 662. The adapter 60 can thus be attached and detached to and from the robot arm 21a more easily.

As illustrated in FIGS. 7 and 8, the arm engagement member 66 includes the engagement member 661, the operating member 662, the bent portion 663, the narrow width portions 664 and 665, and the gripping portion 666, which are integrally formed to one another. The arm engagement member 66 is made of a resin material, for example. The movement of the operating member 662 or the gripping portion 666 causes the plurality of engagement portions 661a to 661c to move in an integrated manner.

The engagement member 661 is at least partially deformable or bendable (for example, elastically or resiliently deformable) such that the engagement portions 661a to 661c are displaceable in the direction from the advanced position to the retracted position. The deformation of the engagement member 661 can improve the dimensional accuracy of the engagement member 661, which allows the engagement portions 661a to 661c to be engaged with reduced backlash.

Specifically, the bent portion 663 is connected to a side of the engagement portion 661a toward the Y2 direction. The bent portion 663 is bent in the Z direction so as to be easily deformed (for example, elastically or resiliently deformed). The bent portion 663 is bent in the Z direction to have two folds. The engagement portion 661a is therefore easily displaceable in the Y direction. The bent portion 663 may be referred to as a deformable portion (for example, an elastically or resiliently deformable portion) for the engagement portion 661a.

The narrow width portion 664 is connected to a side of the engagement portion 661b toward the middle in the X direction. The narrow width portion 664 has a narrow width in the direction intersecting with the extension direction of the narrow width portion 664. The engagement portion 661b is therefore easily deformable in the Y direction. The narrow width portion 664 may be referred to as a deformable portion (for example, an elastically or resiliently deformable portion) of the engagement portion 661b. The narrow width portion 664 is arranged at a position that avoids contact with the electrode array 65.

The narrow width portion 665 is connected to a side of the engagement portion 661c toward the middle in the X direction. The narrow width portion 665 has a narrow width in the direction intersecting with the extension direction of the narrow width portion 665. The engagement portion 661c is therefore easily deformable in the Y direction. The narrow width portion 665 may be referred to as a deformable portion (for example, an elastically or resiliently deformable portion) for the engagement portion 661c. The narrow width portion 665 is arranged at a position that avoids contact with the electrode array 65.

In this manner, the bent portion 663 and the narrow width portions 664 and 665 contribute to easily deforming the engagement member 661.

The gripping portion 666 is provided at an edge portion of the arm engagement member 66 toward the Y2 direction. The gripping portion 666, when pulled in the Y2 direction by an operator, causes the engagement portions 661a to 661c to move in the Y2 direction. The gripping portion 666 is therefore intended to release the engagement portions 661a to 661c from the engaged state. The gripping portion 666 is arranged at a position that avoids contact with the electrode array 65.

The first biasing member 667 is provided at approximately the center of the adapter 60 as viewed in the Z direction. The first biasing member 667 biases the engagement member 66 in the Y1 direction. The first biasing member 667 is comprised, for example, of a spring.

As illustrated in FIG. 5, a plurality of recesses 67 are formed in the first surface 60a of the base 61. That is, the adapter 60 is fixed to the robot arm 21a by the engagement at a plurality of positions. There are four or more recesses 67 provided. This configuration allows the adapter 60 to be attached to the robot arm 21a at four or more engaging positions. The adapter 60 can thus be more stably fixed to the robot arm 21a. For example, there are five recesses 67 provided.

The plurality of recesses 67 are arranged at substantially equal intervals on the outer peripheral side of the first surface 60a. The engaging positions of the adapter 60 with respect to the robot arm 21a are therefore well balanced on the first surface 60a of the adapter 60. The adapter 60 can thus be more stably fixed to the robot arm 21a.

The positioning holes 68 are formed in the first surface 60a. The bosses 214 of the robot arm 21 are fitted in the positioning holes 68. A multiple number of positioning holes 68 are formed. The positioning holes 68 are provided in the vicinity of an edge of the first surface 60a toward the Y1 direction.

Figure 9:
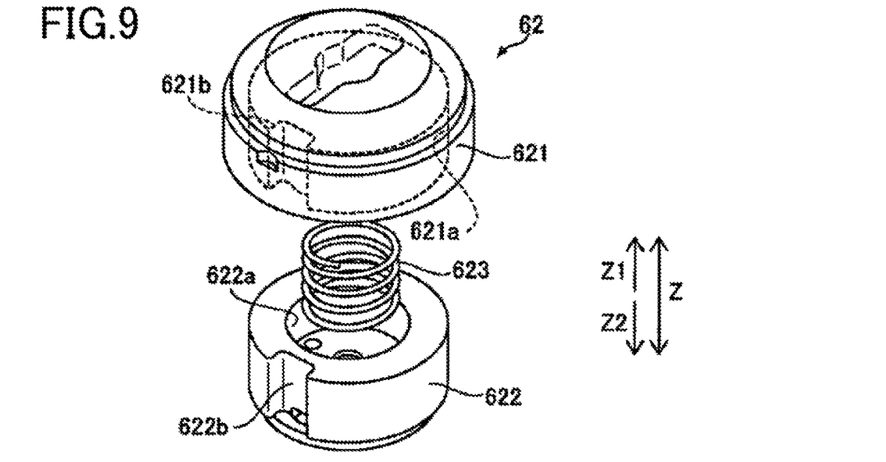
FIG. 9 is a diagram illustrating an exploded perspective view of a drive power transmission member of the adapter according to an embodiment.

As illustrated in FIG. 9, the drive power transmission member 62 includes a first member 621 and a second member 622 movable with respect to the first member 621 via a second biasing member 623. The first member 621 has a recess 621a in which the second member 622 is fitted, and an engaging portion 621b which engages with the second member 622. The second member 622 has a recess 622a which receives the second biasing member 623, and an engaging portion 622b which engages with the first member 621. The first member 621 and the second member 622 are fitted to each other in the Z direction with the second biasing member 623 interposed therebetween. The first member 621 is disposed toward the second surface 60b (toward the Z1 direction). The second member 622 is disposed toward the first surface 60a (toward the Z2 direction). The second biasing member 623 biases the first member 621 in the Z1 direction with respect to the second member 622. The second biasing member 623 is comprised, for example, of a spring.

The second member 622 is flush with the first surface 60a in the Z direction. The second member 622 is disposed so as not to be movable in the Z direction with respect to the base 61. The first member 621 is disposed so as to be movable in the Z direction with respect to the base 61. Thus, in attaching the surgical instrument 40 to the adapter 60, the first member 621 can be depressed in the direction in which the rotational axis of the first member 621 extends (i.e., the Z direction) so as not to inhibit the movement of the surgical instrument 40.

The first member 621 is configured to rotate together with the rotation of the second member 622 about the rotational axis in the Z direction. Specifically, the engaging portion 621b formed on the inner peripheral portion of the first member 621 engages with the engaging portion 622b formed on the outer periphery portion of the second member 622. The engaging portion 621b of the first member 621 protrudes inward from the recess 621a. The engaging portion 622b of the second member 622 is recessed inward from the outer periphery portion of the second member 622. The engaging portion 621b of the first member 621 and the engaging portion 622b of the second member 622 are kept engaged with each other even when the first member 621 moves in the Z direction with respect to the second member 622. That is, the first member 621 is configured to rotate together with the second member 622, irrespective of the position of the first member 621 in the Z direction with respect to the second member 622. Thus, when the second member 622 is rotated by the rotation of the driving member 212 of the robot arm 21, the first member 621 also rotates. The rotation of the driving member 212 of the robot arm 21 is transmitted in this manner to the driven section 44 of the surgical instrument 40 which engages with the first member 621.

Figure 10:
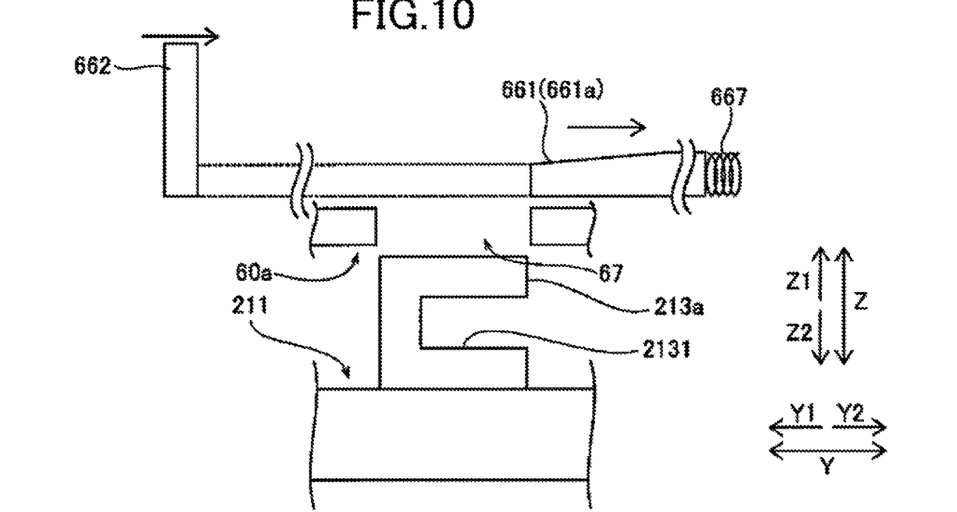
FIG. 10 is a diagram illustrating a view of the state in which an engagement member of the adapter according to an embodiment is moved to a retracted position.
Figure 11:
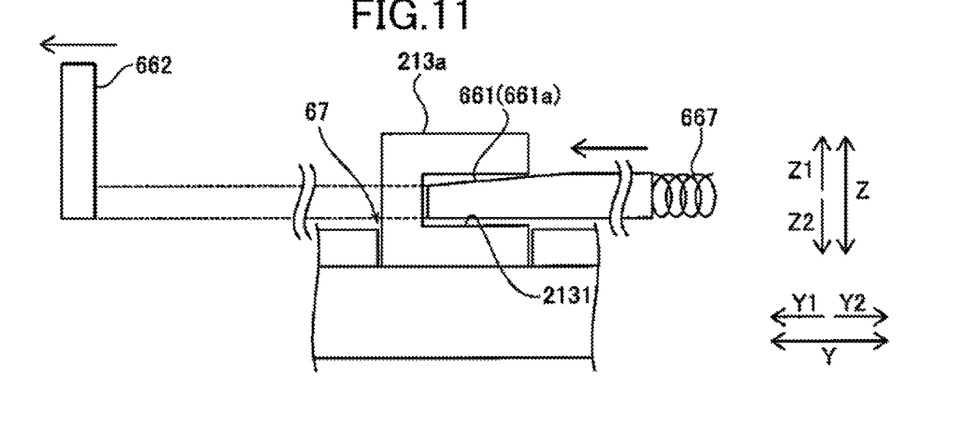
FIG. 11 is a diagram illustrating a view of the state in which the engagement member of the adapter according to an embodiment is moved to an advanced position.

As illustrated in FIGS. 10 and 11, the engagement member 661 is configured such that each of the engagement portions 661a to 661c has a thickness which gradually decreases toward the distal end. This means that the distal end of each of the engagement portions 661a to 661c has an inclined surface. The inclined surfaces of the engagement portions 661a to 661c are inserted in the engagement positions. This configuration allows the engagement portions 661a to 661c to be engaged with reduced backlash without improving the dimensional accuracy of the engagement member 661.

(Attachment of Surgical Instrument to Robot Arm) How to attach the surgical instrument 40 to the robot arm 21a according to an embodiment will be described with reference to FIGS. 12 to 14.

Figure 12:
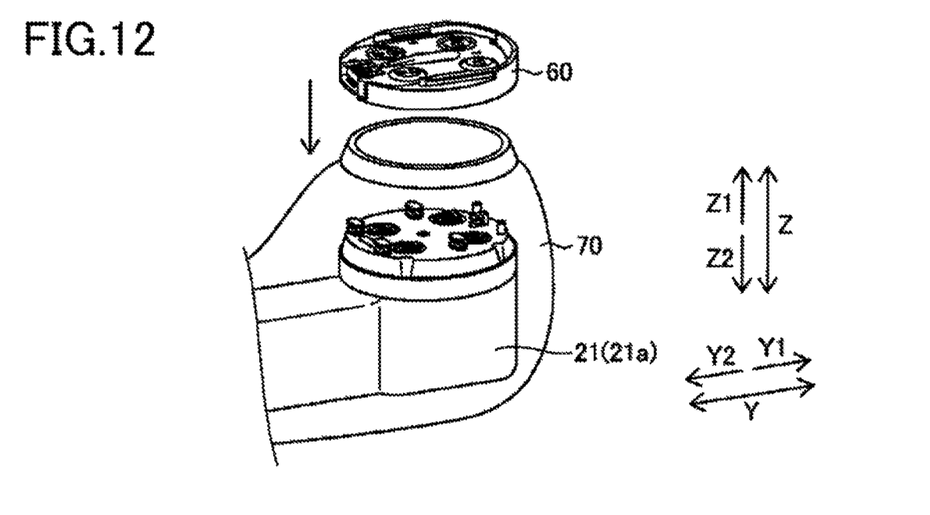
FIG. 12 is a diagram illustrating a view for explaining the attachment of the adapter to the robot arm according to an embodiment.

As illustrated in FIG. 12, the adapter 60 is attached to the robot arm 21a with the drape 70 covering the robot arm 21a. The adapter 60 is moved toward the robot arm 21a in the Z direction and attached to the robot arm 21a. That is, the adapter 60 is moved in the direction perpendicular to the first surface 60a and the second surface 60b (i.e., in the Z direction) to be attached to the attachment portion 211 of the robot arm 21a. Unlike the case in which the adapter 60 is attached to the robot arm 21a by sliding the adapter 60 in the Y direction, the above configuration reduces the possibility that the drape 70 tucked between the adapter 60 and the robot arm 21a is dragged and the drape 70 is deviated from the right position.

Figure 13:
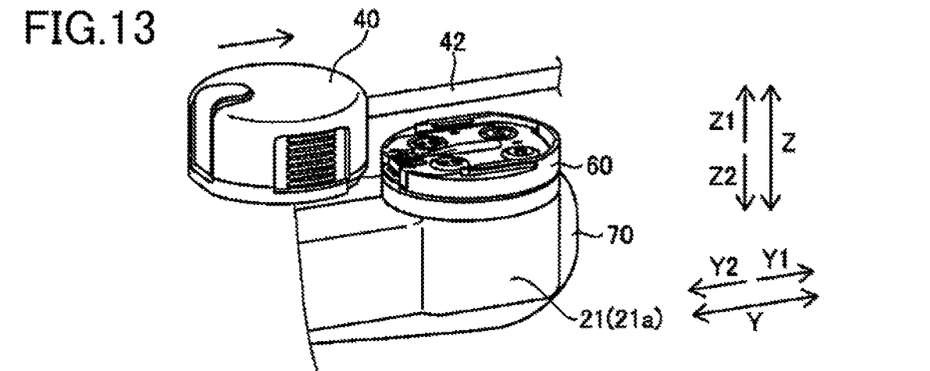
FIG. 13 is a first diagram illustrating a view for explaining the attachment of the surgical instrument to the adapter according to an embodiment.
Figure 14:
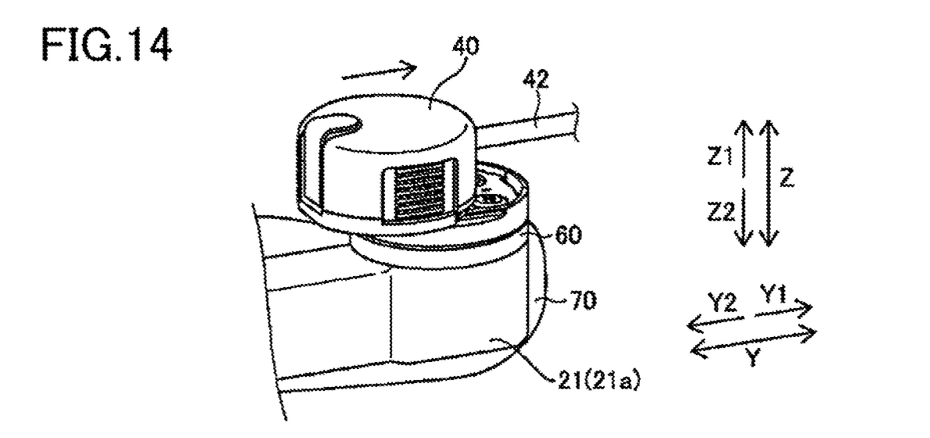
FIG. 14 is a second diagram illustrating a view for explaining the attachment of the surgical instrument to the adapter according to an embodiment.

As illustrated in FIGS. 13 and 14, the surgical instrument 40 is attached to the adapter 60 which has been attached to the robot arm 21a. The surgical instrument 40 is attached to the adapter 60 by moving the surgical instrument 40 in the Y direction along the leading guide rail 64 and the two guide rails 63 of the adapter 60. The surgical instrument 40 is attached to the robot arm 21a via the adapter 60 in this manner.

In detaching the surgical instrument 40 from the robot arm 21a, the surgical instrument 40 is slid in the Y2 direction while pushing the button 461 of the movable member 46 of the surgical instrument 40, thereby detaching the surgical instrument 40 from the adapter 60.

In detaching the adapter 60 from the robot arm 21a, the operating member 662 is pushed in the Y2 direction in the state in which the surgical instrument 40 is detached from the adapter 60, thereby causing the adapter 60 to be disengaged from the robot arm 21a. In this state, the adapter 60 is moved in the Z1 direction, so that the adapter 60 is removed from the robot arm 21a.

(Variations)

The embodiments disclosed herein are meant to be illustrative in all respects and should not be construed to be limiting in any manner. The scope of one or more embodiments is defined not by the above-described embodiments, but by the scope of claims, and includes all modifications (variations) within equivalent meaning and scope to those of the claims.

For example, an example in which the adapter and the attachment portion of the robot arm are engaged with each other by the engagement member at five engaging positions has been described in the above embodiment, but this is a non-limiting example. In one or more embodiments, the adapter and the attachment portion of the robot arm may be engaged with each other by the engagement member at a plurality of engaging positions other than five.

An example in which the adapter has approximately a circular shape in plan view has been described in the above embodiment, but this is a non-limiting example. In one or more embodiments, the shape of the adapter in plan view may not have to be approximately a circular shape. For example, the adapter may have a rectangular shape in plan view.

An example has been described in the above embodiment, in which in the state in which the surgical instrument is attached to the adapter, the movement of the operating member is restricted by the surgical instrument that is in contact with the operating member. This is, however, a non-limiting example. In one or more embodiments, in the state in which the surgical instrument is attached to the adapter, the movement of the operating member may be restricted by anything other than the surgical instrument.

An example in which the adapter has four drive power transmission members has been described in the above embodiment, but this is a non-limiting example. In one or more embodiments, the adapter may have a plurality of drive power transmission members other than four.

An example in which the surgical instrument is attached and detached to and from the adapter by sliding the surgical instrument along the second surface of the adapter has been described in the above embodiment, but this is a non-limiting example. In one or more embodiments, the surgical instrument may be attached and detached to and from the adapter by moving the surgical instrument in a direction different from the direction along the second surface of the adapter. For example, the surgical instrument may be attached and detached to and from the adapter by moving the surgical instrument in a direction perpendicular to the second surface of the adapter.

An example in which the adapter and the drape are independent from each other has been described in the above embodiment, but this is a non-limiting example. In one or more embodiments, the adapter and the drape may be an integrally formed member.

The invention claimed is:

1. An adapter for detachably connecting a surgical instrument to a robot arm of a robotic surgical system, the adapter comprising:
   a base including a first surface to be opposed to and attached to an attachment portion of the robot arm, a second surface different from the first surface, and recesses formed in the first surface, wherein engagement projecting portions projected from the attachment portion of the robot arm are accommodated in the recesses of the base in a state where the first surface of the base of the adapter is attached to the attachment portion of the robot arm;
   one or more drive power transmission members each of which is rotatably provided in the base such that each drive power transmission member is rotatable about a rotational axis thereof to transmit rotation of a corresponding driving member provided in the robot arm, wherein the rotational axis is perpendicular to the first surface;
   an engagement member disposed in the base and movable linearly in a direction perpendicular to the rotational axis between an advanced position where engagement portions of the engagement member are engaged with the engagement projecting portions that are inserted in the recesses respectively and a retracted position where the engagement portions of the engagement member are disengaged from the engagement projecting portions that are inserted in the recesses respectively;
   a biasing member which biases the engagement member in a direction from the retracted position to the advanced position; and
   an operating member to be operated to move the engagement member to the retracted position against a biasing force of the biasing member,
   wherein the engagement member is integrally formed with the engagement portions thereof, and the engagement member is engageable with a groove formed in each of the engagement projecting portions.

2. The adapter of claim 1, wherein
the one or more drive power transmission members comprises drive power transmission members rotatably provided in the base, and
each of the drive power transmission members is configured to transmit rotation of each of driving members, which are provided to the attachment portion of the robot arm, to driven sections provided to the surgical instrument.

3. The adapter of claim 1, wherein
movements of the engagement member by the operating member are restricted in a state in which the first surface is attached to the attachment portion of the robot arm and the surgical instrument is attached to the second surface.

4. The adapter of claim 1, wherein
the operating member is configured to move the engagement portions in an integrated manner.

5. The adapter of claim 2, wherein
each of the drive power transmission members is provided rotatable about the rotational axis thereof perpendicular to the first surface and the second surface, and includes a first member and a second member movable with respect to the first member with a second biasing member between the first member and the second member.

6. The adapter of claim 1, wherein
the number of the recesses is four or more.

7. An adapter for detachably connecting a surgical instrument to a robot arm of a robotic surgical system, the adapter comprising:
   a base including a first surface to be opposed to and attached to an attachment portion of the robot arm, a second surface different from the first surface, and recesses formed in the first surface, wherein engagement projecting portions projected from the attachment portion of the robot arm are accommodated in the recesses of the base in a state where the first surface of the base of the adapter is attached to the attachment portion of the robot arm;
   one or more drive power transmission members each of which is rotatably provided in the base such that each drive power transmission member is rotatable about a rotational axis thereof to transmit rotation of a corresponding driving member provided in the robot arm, wherein the rotational axis is perpendicular to the first surface;
   an engagement member disposed in the base and movable linearly in a direction perpendicular to the rotational axis between an advanced position where engagement portions of the engagement member are engaged with the engagement projecting portions that are inserted in the recesses respectively and a retracted position where the engagement portions of the engagement member are disengaged from the engagement projecting portions that are inserted in the recesses respectively;
   a biasing member which biases the engagement member in a direction from the retracted position to the advanced position; and
   an operating member to be operated to move the engagement member to the retracted position against a biasing force of the biasing member,
   wherein the engagement member is integrally formed with the engagement portions thereof, and the engagement member is configured such that each of the engagement portions has a thickness which gradually decreases toward a distal end of the engagement portion.

8. The adapter of claim 1, wherein
the engagement member is at least partially deformable such that each of the engagement portions is displaceable in a direction from the advanced position toward the retracted position.

9. The adapter of claim 8, wherein
the engagement member includes a deformable portion having at least one of a bended portion and a narrow width portion of the engagement member.

10. The adapter of claim 1, wherein
the adapter is moved in a direction perpendicular to the first surface and the second surface to be attached to the attachment portion of the robot arm.

11. The adapter of claim 1, wherein
the adapter is attached to the attachment portion of the robot arm with a drape interposed between the adapter and the attachment portion of the robot arm.

12. A surgical instrument set comprising:
an adapter to be attached to a robot arm of a robotic surgical system; and
a surgical instrument to be attached to the adapter,
the adapter including
   a base including a first surface to be attached to an attachment portion of the robot arm, a second surface different from the first surface and formed with a guide rail thereon, and recesses formed in the first surface, wherein engagement projecting portions projected from the attachment portion of the robot arm are accommodated in the recesses of the base in a state where the first surface of the base of the adapter is attached to the attachment portion of the robot arm,
   one or more drive power transmission members each of which is rotatably provided in the base such that each drive power transmission member is rotatable about a rotational axis thereof to transmit rotation of a driving member provided in the robot arm, wherein the rotational axis is perpendicular to the first surface,
   an engagement member disposed in the base and movable linearly in a direction perpendicular to the rotational axis between an advanced position where engagement portions of the engagement member are engaged with the engagement projecting portions that are inserted in the recesses respectively and a retracted position where the engagement portions of the engagement member are disengaged from the engagement projecting portions that are inserted in the recesses respectively,
   a biasing member which biases the engagement member in a direction from the retracted position to the advanced position, and
   an operating member to be operated to move the engagement member to the retracted position against a biasing force of the biasing member, wherein
the surgical instrument includes an attachment surface to be attached to the second surface of the adapter and a guide groove in the attachment surface, the guide groove receiving the guide rail on the second surface of the adapter, and
the engagement member is integrally formed with the engagement portions thereof.

13. The surgical instrument set of claim 12, wherein
the one or more drive power transmission members comprises drive power transmission members rotatably provided in the base,
the surgical instrument includes driven sections, and
each of the drive power transmission members is configured to transmit rotation of each of driving members, which are provided to the attachment portion of the robot arm, to the driven sections of the surgical instrument.

14. A surgical instrument set comprising:
an adapter to be attached to a robot arm of a robotic surgical system; and
a surgical instrument to be attached to the adapter,
the adapter including
   a base including a first surface to be attached to an attachment portion of the robot arm, a second surface different from the first surface, and recesses formed in the first surface, wherein engagement projecting portions projected from the attachment portion of the robot arm are accommodated in the recesses of the base in a state where the first surface of the base of the adapter is attached to the attachment portion of the robot arm,
   one or more drive power transmission members each of which is rotatably provided in the base such that each drive power transmission member is rotatable about a rotational axis thereof to transmit rotation of a driving member provided in the robot arm, wherein the rotational axis is perpendicular to the first surface,
   an engagement member disposed in the base and movable linearly in a direction perpendicular to the rotational axis between an advanced position where engagement portions of the engagement member are engaged with the engagement projecting portions that are inserted in the recesses respectively and a retracted position where the engagement portions of the engagement member are disengaged from the engagement projecting portions that are inserted in the recesses respectively,
   a biasing member which biases the engagement member in a direction from the retracted position to the advanced position, and
   an operating member to be operated to move the engagement member to the retracted position against a biasing force of the biasing member, wherein
the surgical instrument includes an attachment surface to be attached to the second surface of the adapter, and
the engagement member is integrally formed with the engagement portions thereof and the engagement member is engageable with a groove formed in each of the engagement projecting portions.

15. A method for detachably connecting a surgical instrument to a robot arm of a robotic surgical system via an adapter,
the adapter comprising:
a base including a first surface to be attached to an attachment portion of the robot arm, a second surface to which an attachment surface of the surgical instrument is attached, and recesses formed in the first surface, wherein engagement projecting portions projected from the attachment portion of the robot arm are accommodated in the recesses of the base in a state where the first surface of the base of the adapter is attached to the attachment portion of the robot arm;
one or more drive power transmission members each of which is rotatably provided in the base such that each drive power transmission member is rotatable about a rotational axis thereof to transmit rotation of a driving member provided in the robot arm, wherein the rotational axis is perpendicular to the first surface;

an engagement member movable linearly in a direction perpendicular to the rotational axis between an advanced position where engagement portions of the engagement member are engaged with the engagement projecting portions that are inserted in the recesses respectively and a retracted position where the engagement portions of the engagement member are disengaged from the engagement projecting portions that are inserted in the recesses respectively;

a biasing member which biases the engagement member in a direction from the retracted position to the advanced position; and an operating member to be operated to move the engagement member to the retracted position against a biasing force of the biasing member, wherein the engagement member is integrally formed with the engagement portions thereof, wherein the adapter includes a guide rail on the second surface, and the surgical instrument includes a guide groove in the attachment surface, the guide groove receiving the guide rail, the method comprising:

moving the engagement member to the retracted position with the operating member;

attaching the first surface of the adapter in which the engagement member has been moved to the retracted position, to the attachment portion of the robot arm;

moving the engagement member to the advanced position by the biasing member; and attaching the attachment surface of the surgical instrument to the second surface of the adapter.

16. The method of claim 15, wherein the one or more drive power transmission members comprises drive power transmission members rotatably provided in the base, the surgical instrument includes driven sections, and each of the drive power transmission members is configured to transmit rotation of each of driving members, which are provided to the attachment portion of the robot arm, to the driven sections of the surgical instrument in a state where the attachment surface of the surgical instrument is attached to the second surface of the adapter.

* * * * *